United States Patent [19]

Berkner

[11] Patent Number: 5,084,614

[45] Date of Patent: Jan. 28, 1992

[54] OPTICAL SINGLE PARTICLE DETECTOR WITH LENSELESS FIBER OPTIC PROBE

[75] Inventor: Lawrence S. Berkner, Minneapolis, Minn.

[73] Assignee: TSI Incorporated, St. Paul, Minn.

[21] Appl. No.: 586,239

[22] Filed: Sep. 21, 1990

[51] Int. Cl.$^5$ .......................... H01J 5/16; H01J 40/14
[52] U.S. Cl. ............................... 250/227.11; 250/574; 356/336
[58] Field of Search .................. 250/227.11, 573, 574; 356/336–338, 441, 442

[56] References Cited

U.S. PATENT DOCUMENTS

| | | | |
|---|---|---|---|
| 3,899,688 | 8/1975 | Périères | 356/442 |
| 4,072,424 | 2/1978 | McMullan et al. | 356/442 |
| 4,260,258 | 4/1981 | Rose et al. | 250/573 |
| 4,492,868 | 1/1985 | Jelvestam et al. | 356/441 |
| 4,629,903 | 12/1986 | Giacobbe et al. | 250/227.11 |
| 4,752,131 | 6/1988 | Eisenlauer et al. | 356/442 |
| 4,804,853 | 2/1989 | Borden et al. | 250/574 |
| 4,827,143 | 5/1989 | Munakata et al. | 250/574 |
| 4,842,406 | 6/1989 | Von Bargen | 356/336 |
| 4,890,920 | 1/1990 | Niziolek et al. | 356/336 |
| 4,893,935 | 1/1990 | Mandel et al. | 356/442 |
| 4,896,048 | 1/1990 | Borden | 250/574 |
| 4,906,101 | 3/1990 | Lin et al. | 356/442 |

*Primary Examiner*—David C. Nelms
*Assistant Examiner*—S. Allen
*Attorney, Agent, or Firm*—Haugen and Nikolai

[57] ABSTRACT

An instrument for detecting single airborne particles, and measuring their concentration, includes a transmitting optical fiber optically connected to a light source at one end, and a collecting optical fiber connected to a photodiode at one of its ends. The respective opposite ends of the optical fibers are potted into a rigid probe head with their exposed ends polished smooth and flat, facing each other and separated by an air gap of about one-tenth of an inch. At least some of the light from the source crosses the gap between the optical fibers and reaches the detector, such portion of the light defining a particle sensing volume. Particles passing through this volume are detected by optical extinction as they reduce the amount of light reaching the detector. The device has simple optics, requiring no lenses or mirrors. The transmitting and collecting fibers, and the air gap, form a well defined and repeatable sensing volume so that individual devie calibration is not required. The probe is small and rugged, allowing it to be inserted directly in a fluid flow for in-situ measurements even in hostile environments. Associated signal processing electronics account for fluid stream velocity, so that the device measures true aerosol concentration in a fluid stream, regardless of changes in the stream velocity. The particle size threshold in the electronics is a percentage of the light to the detector which allows to remain in calibration when the amount of light through the probe changes.

16 Claims, 5 Drawing Sheets

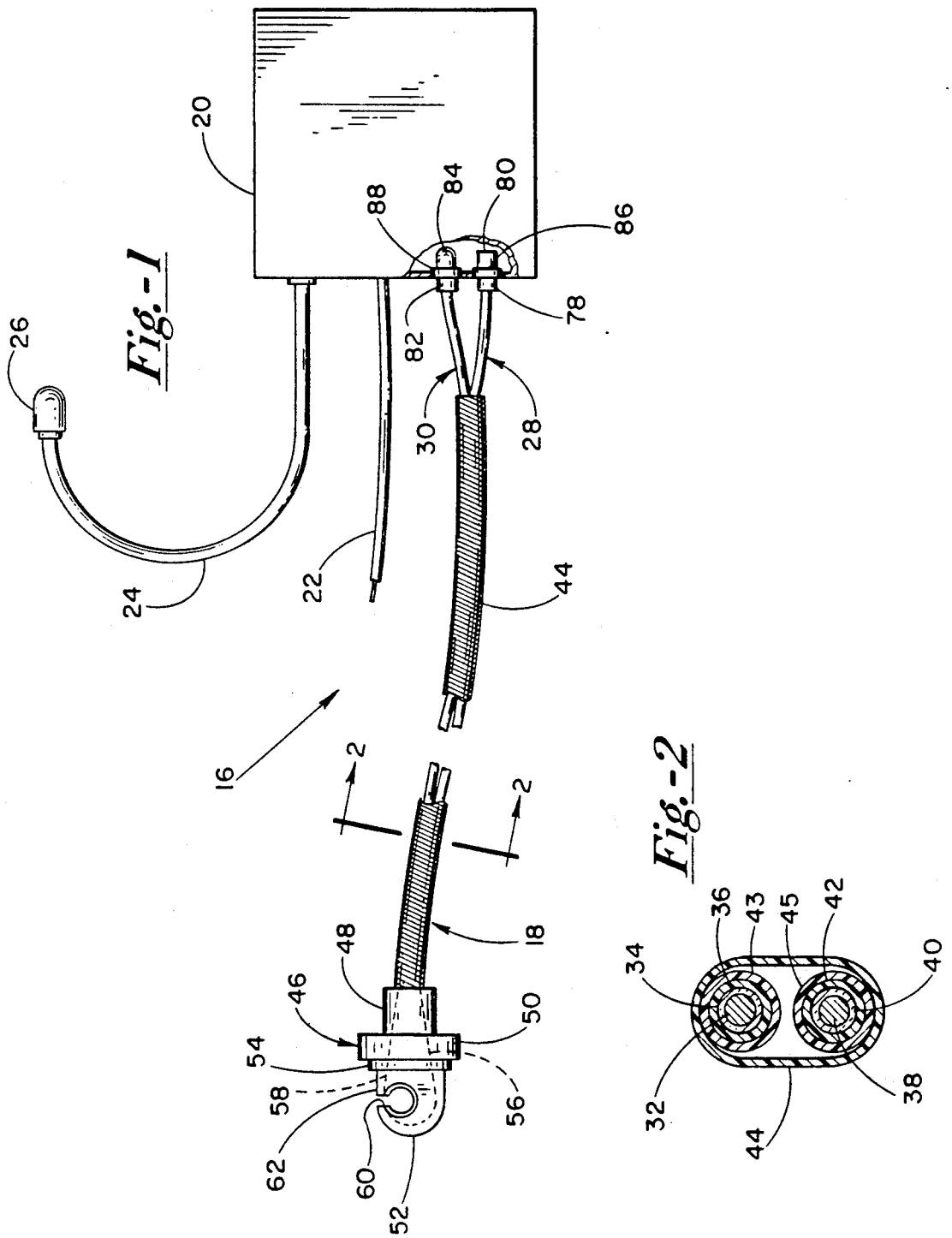

OPTICAL SINGLE PARTICLE DETECTOR WITH LENSELESS FIBER OPTIC PROBE

The United States Government has contributed to the design and development of the invention herein, and accordingly has acquired ownership of certain rights in the invention.

BACKGROUND OF THE INVENTION

The present invention relates to devices for determining the concentration of fine particles suspended in air or another fluid, and more particularly to optical single particle detectors.

A wide variety of instruments are available for measuring the size and concentration of airborne particulates, for purposes as divergent as monitoring air pollution, measuring the effectiveness of filters in ventilation systems and elsewhere, and determining particle concentrations in liquids. Optical systems are frequently employed in these situations because they enable non-intrusive particle measurement and provide real time data. Such devices include photometers, which measure the total light scattered from many particles at once, and single particle detectors.

Single particle detectors provide more precise information on particle concentration and size distribution, and are superior to photometers in measuring low concentrations. Such instruments detect particles either by light scattering or by light extinction. Light scattering involves measuring light that a particle refracts, diffracts or re-radiates, at an angle or range of angles different than the original direction of the light. The extinction method involves continuously measuring light from a source to a detector. When a particle passes through the light, it decreases the amount of light reaching the detector, with larger particles diminishing light to a greater degree.

Whether they rely on light scattering or extinction, single particle detectors are complex and expensive. In both cases, precision optics are necessary to create a tiny, high intensity light spot. This maximizes the amount of light scattered from or blocked by a single particle. Extinction systems sometimes pass particles through the resonant cavity of a gas laser, to provide a higher intensity light beam.

In either type of system, knowing or controlling the volume of air containing the aerosol is essential for an accurate measurement of concentration. Generally this is done with a sampling pump, which draws air through the light beam at a constant rate.

While presently available single particle detectors are suitable in a wide variety of applications, they are not well suited to certain needs in industry. Most of the current technology is geared towards detecting the smallest particle possible. For example, earth moving vehicles and other construction equipment frequently are subjected to harsh environments involving dust, temperature extremes, vibration and shock. The internal combustion engines running this equipment can be destroyed in minutes by unduly high particulate concentrations in the engine intake air. Thus, the ability to provide an early warning of potentially damaging aerosol concentrations is critical.

Currently available measurement approaches, however, are not suited to this end. Particulate concentrations downstream of a properly functioning air filter are substantially lower than concentrations appropriate for photometers. Yet single particle optical systems require precision optics with several lenses. Components of the device must be aligned, and usually each completed device must be individually calibrated due to the unique shape of its optical particle sensing volume. The relatively large size of certain optical system components generally prevent the system from being installed directly in the fluid flow. The sampling system, needed to draw aerosol into the sensing volume, adds to the cost of the instrument. Sampling decreases accuracy, because particles are lost to the sampling tube walls as the aerosol is drawn by the sampling pump. These optical sensing systems lack sufficient structural rigidity for installation in hostile environments involving shock, vibration and temperature extremes.

Therefore, it is an object of the present invention to provide a single particle detecting device with a small in-situ probe that can be mounted directly in an aerosol flow.

Another object is to provide a single particle detecting device which requires no lenses, mirrors or other precision optics, and further requires no alignment or calibration, yet provides a well defined, repeatable particle sensing volume.

A further object is to provide a single particle detection device which is sufficiently rugged to perform reliably in harsh environments.

Yet another object of the invention is to provide a single particle detection device for measuring concentrations independently of the velocity of the air stream in which the particles are suspended.

SUMMARY OF THE INVENTION

To achieve these and other objects, there is provided an apparatus for detecting single particles in a fluid stream. The apparatus includes a transmitting fiber optic means and a collecting fiber optic means, each having first and second opposite ends. A light source is optically coupled to the first end of the transmitting fiber optic means. A light detecting means is optically coupled to the first end of the collecting fiber optic means. A mounting means maintains the transmitting and collecting fiber optic means, substantially fixed along respective end portions of the fiber optic means to position their respective second ends within a fluid stream, confronting one another and spaced apart longitudinally from one another to define a gap in the fluid stream. At least a portion of the light exiting the transmitting fiber optic means crosses the gap and is received by the collecting fiber optic means for transmission to the detecting means. This portion of the light defines a particle sensing volume spanning the gap. A signalling means is coupled to the light detecting means, for generating a particle indicating signal proportional to the amount of light sensed by the detecting means.

Preferably the indicating signal is an analog voltage signal having a nominal voltage level when the particle sensing volume is free of particles. The voltage level is less than the nominal level whenever a particle suspended in the fluid stream occupies the particle sensing volume, and thereby temporarily diminishes the amount of light received by the collecting fiber optic means.

A threshold voltage, less than the nominal voltage and preferably proportional to the nominal voltage, can be compared with the analog voltage signal. When the analog voltage signal goes below the threshold, this indicates a particle above a certain size has been detected. Using this information, an alarm can be activated, indicating an undesirably high level of particulate concentration in the fluid stream.

In the preferred arrangement, the fiber optic means comprise respective first and second elongate and cylindrical optical fibers, axially aligned with one another and substantially equal in diameter. Each of the confronting second ends is substantially flat, smooth and transverse. As a result, light diverges as it exits the transmitting optical fiber, the proportion of light collected being determined by the longitudinal gap between the fibers and the fiber diameters. The diameters and gap dimension further define the particle sensing volume, which in the preferred arrangement is a cylinder with its axis or longitudinal dimension perpendicular to the direction of the fluid stream.

In alternative arrangements, the collecting optical fiber can receive substantially all light emitted by the transmitting fiber, due to contouring the transmitting fiber second end to reduce divergence or collimate the light beam across the gap, or alternatively to provide a collecting optical fiber substantially larger in diameter than the transmitting fiber. Regardless of comparative fiber size, substantially flat second edges are preferred, particularly when co-planar with surrounding portions of the casing or other mounting means. This enhances useful life of the probe by reducing the probability of particulate soiling of the fiber ends, which would reduce the passage of light across these ends.

Salient features of the present invention include the ability to set a minimum size of particle that will trigger the sensing device, and to accurately sense concentrations regardless of changes in air stream velocity. Generally, a particle in the particle sensing volume diminishes the passage of light (and thus reduces the detector voltage level) in proportion to its size. Accordingly, the voltage threshold can be set to determine minimum particle size to be sensed in determining concentrations.

A particle sensing device in accordance with the present invention has a simplified optic design which substantially reduces its cost. There are no lenses, mirrors or other optical elements to install, align or adjust. The transmitting and collecting fibers provide the only required optical elements. When mounted in the probe casings, the fibers form a well defined and repeatable particle sensing volume. There is no need to align or calibrate individual probes, thus further reducing cost.

The small size of the probe, compared to conventional single particle detectors, allows installation of the probe directly in the fluid stream for in-situ measurements with minimal interference with the fluid flow. This eliminates the need for an air sampling system, for better sampling accuracy and reduced cost and complexity. The probe casing can substantially surround the optical fibers, resulting in a rugged probe capable of withstanding temperature extremes, shock and vibration found in engine intake air ducts and in other hostile environments.

Particle concentration is measured, based upon the number of particles occupying the sensing volume over a predetermined time span, and the amount of time each particle occupies the sensing volume. Variations in fluid stream velocity alter both of these factors, increasing one while decreasing the other. The result is a balance, which give consistent particle concentration readings in spite of changes in stream velocity.

The particle measuring threshold is a constant percentage of the light across the particle sensing volume in the absence of particles. Consequently the probe calibration is maintained, regardless of variations in the nominal level of light across the sensing volume, caused for example by a diminishing output of the light source. However, should the light source output fall below a minimally acceptable level, a low level signal is provided, indicating the need for inspection.

IN THE DRAWINGS

For a further appreciation of the above and other features and advantages, reference is made to the following detailed description and to the drawings, in which:

FIG. 1 illustrates a single particle detecting device constructed in accordance with the present invention;

FIG. 2 is a sectional view taken along the line 2—2 in FIG. 1;

Figure 10:
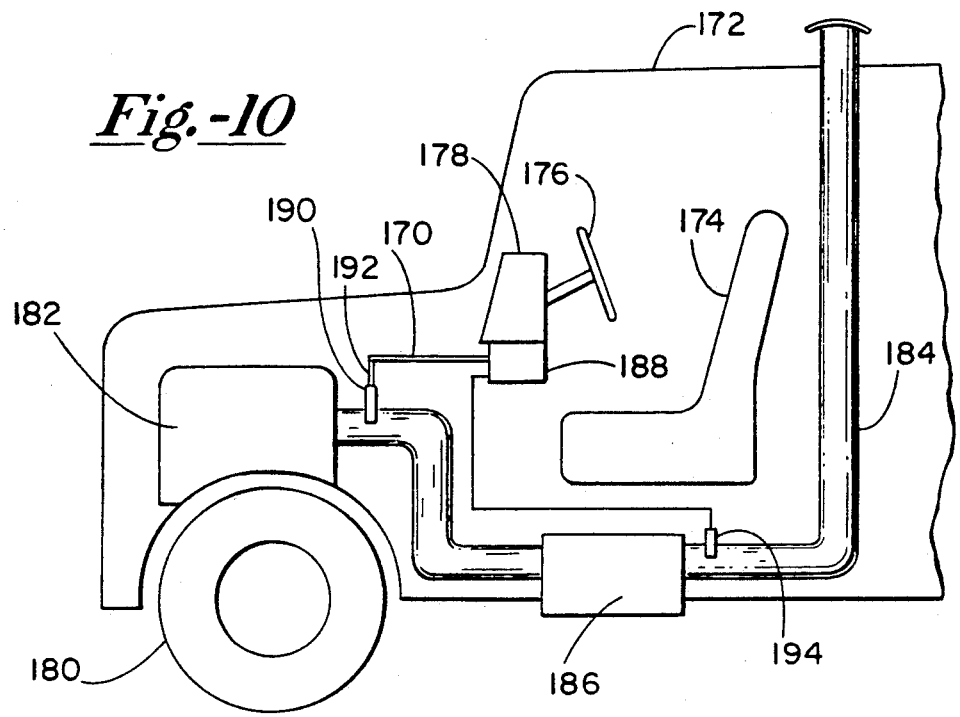
Figure 11:
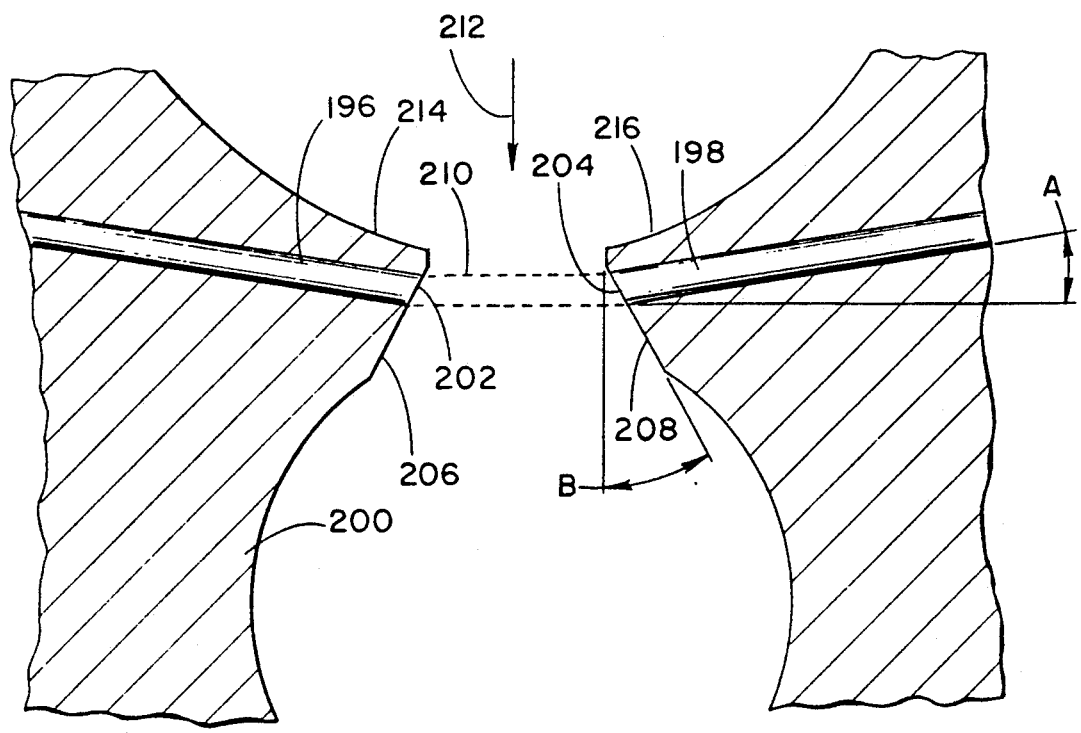

FIG. 10 diagrammatically illustrates a particle sensing system in accordance with the present invention, installed in a road construction vehicle; and FIG. 11 illustrates an alternative embodiment single particle detecting device.

DETAILED DESCRIPTION OF THE PREFERRED EMBODIMENTS

Turning now to the drawings, there is shown in FIG. 1 a single particle sensing device 16 for measuring concentrations of particulates or aerosols suspended in an air flow or other fluid stream. The device includes an optical probe 18 and an electronics package 20 that contains the signal processing circuitry coupled to the probe. An input line 22 provides DC power to electronic package 20, and an electrical line 24 couples circuitry in the package to an alarm indicator light 26.

Probe 18 includes two optical fibers, a transmitting optical fiber 28 and a collecting optical fiber 30. As seen in FIG. 2, transmitting fiber 28 has a cylindrical glass core 32 with a diameter of 200 microns, surrounded by a glass cladding 34, in turn surrounded by compliant silicone buffer layer 36. Collecting fiber 30 likewise includes a 200 micron diameter glass core 38, cladding 40 and a buffer layer 42. Respective coverings 43 and 45 surround buffer layers 36 and 42. Each covering includes a woven fiber layer (e.g. as sold under the brand name Kevlar) surrounding the buffer layer, and in turn surrounded by a polymeric layer. A protective outer jacket 44 surrounds both of the optical fibers over the majority of their length. Outer jacket 44 is preferably a plastic, of suitable rigidity to afford mechanical protection for the optical fibers, yet sufficiently compliant to permit bending of the jacket and fibers into a curved or serpentine path, if desired or necessary.

Returning to FIG. 1, probe 18 includes a rigid probe head 46, preferably formed of aluminum. The probe head includes a neck 48 surrounding outer jacket 44, a mounting flange 50 used to secure the probe head to a duct or other rigid structure enclosing the fluid stream, and a hook-shaped casing 52. An elastically compressible polymer layer 54 is applied to one side of mounting flange 50, to improve the seal of the flange against an outer wall of a duct (for example), with casing 52 protruding into the duct through a opening in the duct wall.

Figure 3:
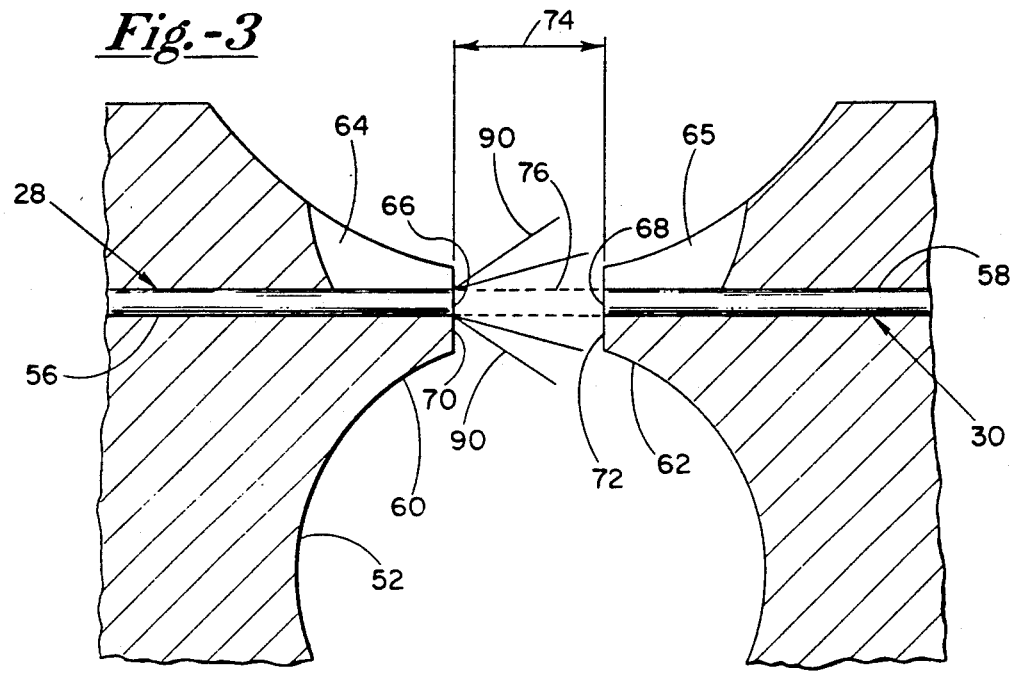
FIG. 3 is an enlarged view of a portion of FIG. 1.

Channels and tunnels are formed in probe head 46 to accommodate and align respective proximal end regions 56 and 58 of optical fibers 28 and 30. More particularly, the optical fibers are stripped of coverings 43 and 45 to expose their proximal ends, which are then routed into the probe head at neck 48. The proximal end region 58 of collecting fiber 30 is channelled directly to one of two spaced apart and opposed tapered regions of casing 52, indicated at 62 (FIG. 3). The proximal end region 56 of the transmitting fiber is mounted in a channel along the outer radius of the casing, forms an approximately 180 degree bend, and terminates at tapered region 60 of the casing.

Troughs 64 and 65 are formed in the casing at tapered portions 60 and 62, respectively. Along the troughs, proximal end portions 56 and 58 of the optical fibers are stripped of their respective buffer layers to expose the cladding. When laid in troughs 64 and 65, the exposed end portions of the fibers are axially aligned and face each other. When so positioned, they are glued permanently into place with an epoxy. The rest of each proximal end portion is similarly potted within its associated openings or channels, to permanently secure these portions to the probe head.

Preferably the exposed end portions of the fibers, when secured within troughs 64 and 65, extend longitudinally (i.e. axially of the fibers) beyond the casing. Each of the end portions then is cleaved and polished to a flat, smooth and transverse end or face, as indicated at 66 and 68 for fibers 28 and 30, respectively. A smooth finish is particularly important for maximum light transmission. Tapered region 60 of the casing includes a flat, transverse surface 70 surrounding and co-planar with face 66. Likewise, a transverse surface 72 of the casing is co-planar with face 68. Thus, a longitudinal gap 74 is formed between the two flat, smooth and transverse faces, as best seen in FIG. 3. The gap width (i.e. the longitudinal dimension) preferably is about one-tenth of an inch. The gap width, along with the 200 micron diameter of fiber cores 32 and 38, defines a cylindrical particle sensing volume, indicated at 76 by broken lines in FIG. 3.

Returning to FIG. 1, an optical connector 78 couples transmitting fiber 28 with a light emitting diode (LED) 80 or another suitable light source. Similarly an optical connector 82 couples collecting fiber 30 with a detector 84, preferably a silicon PIN photodiode. LED 80 and detector 84 are mounted in respective receptacles 86 and 88, each of which extends outside of electronics package 20 to releasably receive one of connectors 78 and 82.

Thus, an optical path is formed from LED 80 to detector 84, including connector 78, transmitting optical fiber 28, gap 74, collecting optical fiber 30 and connector 82. LED 80 sends a constant amount of light into transmitting fiber 28. This light exits the transmitting fiber as a diverging beam, the boundaries of which are indicated by solid lines at 90. Approximately two percent of the light remains within particle sensing volume 76, and enters collecting fiber 30 after crossing gap 74. This collected light travels to detector 84, which generates a DC voltage level proportional to the amount of light it receives.

Figure 4:
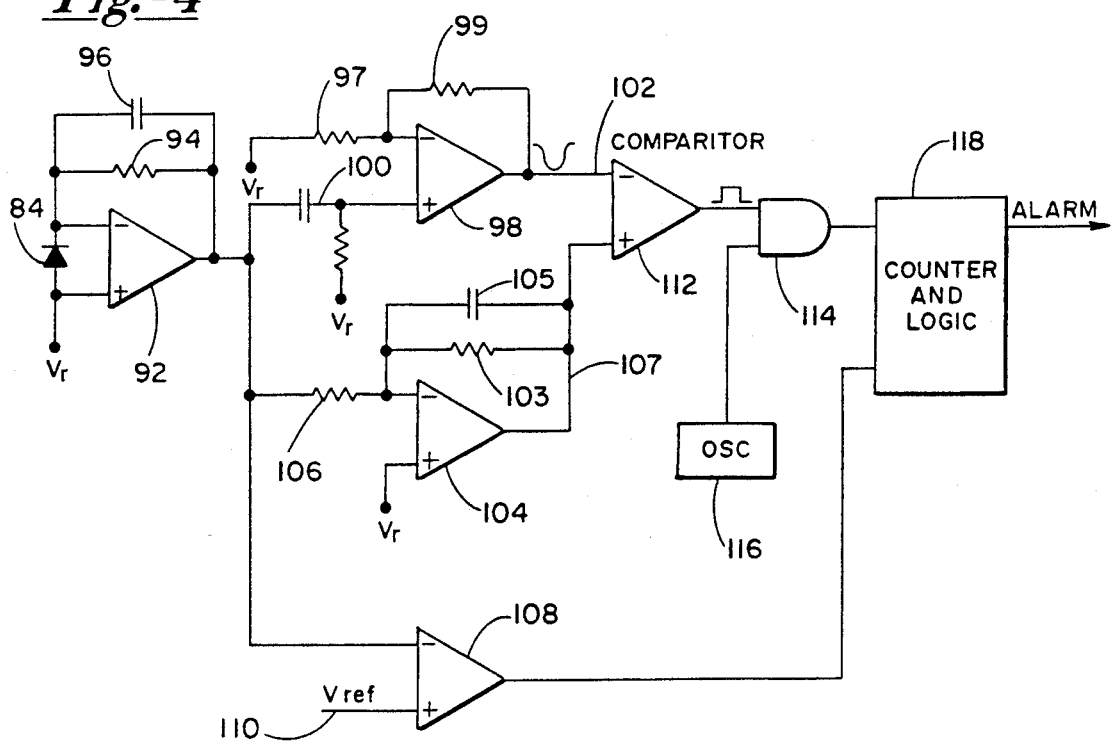
FIG. 4 is a schematic view of a signal processing circuit of the device.

FIG. 4 illustrates the electronic circuitry for providing particle concentration information, based on the voltage output of detector 84. An operational amplifier 92, having a gain control circuit including a resistance 94 and a capacitance 96, converts the current from detector 84 to a voltage level at its output. The output of amplifier 92 is provided to the positive input terminal of an operational amplifier 98, through an R.C. filter 100 which filters out low frequency responses. The negative input terminal of amplifier 98 receives a reference voltage $V_r$ across a resistance 97. The gain control circuit of the amplifier includes a resistance 99. The output of amplifier 98 is a filtered and amplified analog voltage, i.e. a particle indicating signal 102.

The output of amplifier 92 also is provided to the negative terminal of an operational amplifier 104, through a resistance 106. The positive input terminal of amplifier 104 is connected to reference voltage $V_r$. Amplifier 104 has a gain control circuit including a resistance 103 and a capacitance 105. Resistance 103 (or alternatively resistance 106) is selected to provide a threshold voltage level 107 as the output of amplifier 104, less than and substantially linearly proportional to the output of amplifier 92. More precisely, the difference between voltage level 107 and $V_r$ is linearly proportional to the difference between the output of amplifier 92 and $V_r$. The proportional, linear relationship results from the selection of resistances 97, 99, 103 and 106. More particularly, the resistance 99 is ten times resistance 97, to provide a factor of ten gain in the AC signal. By contrast, resistance 106 is approximately sixteen times resistance 103, and a relatively high capacitance is provided in the feedback loop at 105. Consequently, the output of amplifier 104 reflects the stable DC signal rather than the AC fluctuations. The following values have been found satisfactory in the circuit shown in FIG. 4:

Resistance 94: 400 k ohms
Resistance 97: 1.33 k ohms
Resistance 99: 13.3 k ohms
Resistance 103: 6.34 k ohms
Resistance 106: 100 k ohms
Capacitance 96: 5.6 pf
Capacitance 105: 10 $\mu$f Finally, the output of amplifier 92 is provided to the negative terminal of a comparator 108. A constant reference voltage 110 is provided to the positive terminal of comparator 108. Whenever the output of amplifier 92 is a voltage less than the reference voltage, the output of comparator 108 is a "high" logic level, this output otherwise being a low logic level.

A comparator 112 receives the output 102 of amplifier 98 and threshold voltage 107, at its negative and positive input terminals respectively. Accordingly, the comparator generates a low logic level output so long as signal 102 remains above threshold voltage 107. Whenever signal 102 drops below the threshold voltage, comparator 112 generates the high logic level and provides the high level to an AND logic gate 114. AND gate 114 also receives a one MHz pulse from a 1MHz oscillator 116. When receiving the high input, AND gate 114 provides an enabling signal to a counter and alarm control circuit 118. This enabling signal essentially replicates the one megahertz pulse stream input to the AND gate. The other signalling input to circuit 118 is the output of comparator 108 which, when high, causes circuit 118 to trigger an alarm indication that the light being received by detector 84 is insufficient for particle concentration measurement, e.g. due to a broken optical fiber, failed LED or dirty optical faces.

As previously mentioned, all light received into collecting fiber 30 for detector 84 passes through particle sensing volume 76, which is determined by the 0.1 inch gap width and the 200 micron diameter of the optical fiber cores. When an airborne particle is within the sensing volume, it scatters and absorbs some of the light which otherwise would reach detector 84. This decreases the voltage level of particle signal 102, i.e. superimposes negative voltage pulses onto the nominal DC voltage level, to provide a varying particle responsive measurement signal.

Figure 5:
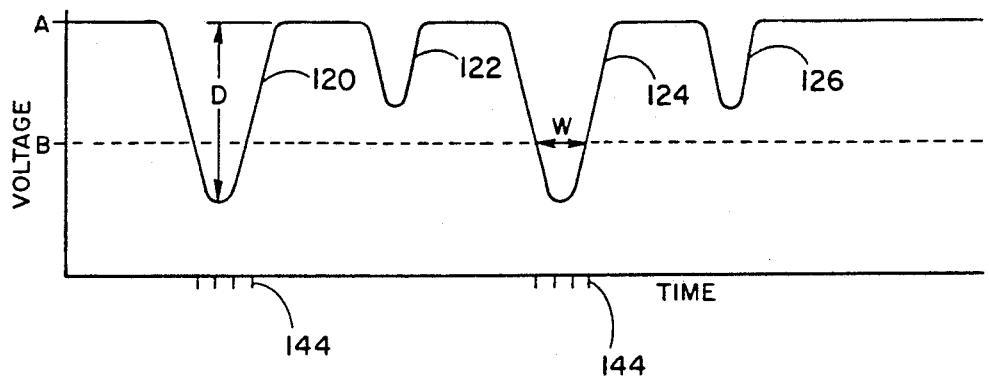
FIGS. 5 and 6 illustrate comparative analog voltage outputs at different air stream velocities.
Figure 6:
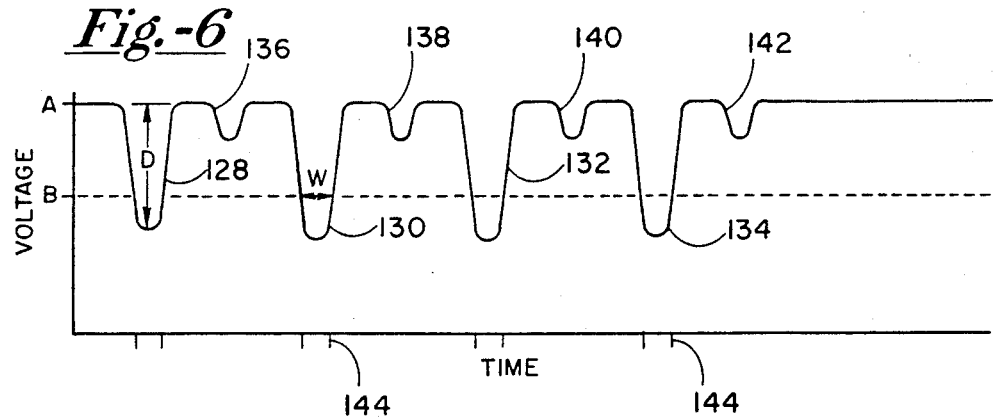

FIGS. 5 and 6 illustrate particle measurement signals for fluid streams of different velocities. In each case the nominal voltage level, corresponding to particle sensing volume 76 being free of particles, is indicated at "A", and the threshold voltage is indicated at "B". Each of pulses 120-126 (FIG. 5) corresponds to a particle in the fluid stream passing through the sensing volume. The depth of each pulse, e.g. D in connection with pulse 120, corresponds substantially to the particle size and more particularly to the particle profile, i.e. the cross sectional area in a plane perpendicular to the width of gap 74. Pulses 120 and 124 are "triggering pulses" in the sense that they reduce the measurement signal below threshold level 107. Pulses 122 and 126 are non-triggering pulses caused by smaller particles. It is to be appreciated that resistance 106 (FIG. 4) can be selected as desired, either to increase or decrease threshold 107, thus to decrease or increase the minimum particle size triggering the system.

In FIG. 6, the measurement signal includes four triggering pulses 128-134 similar in depth to pulses 120 and 124, and four non-triggering pulses 136-142. FIG. 6 corresponds to a fluid stream in which the particle concentration and size distribution is the same as that corresponding to FIG. 5. However, the fluid stream velocity in FIG. 6 is twice that in FIG. 5. In each case the pulse width, indicated at W in connection with pulses 124 and 130, is proportional to the time the particle occupies the sensing volume, i.e. inversely proportional to particle velocity through the sensing volume. For the duration in which any pulse is below threshold B, 1 MHz oscillator 116 is enabled to generate triggering counts. The number of counts is linearly proportional to the width of the pulse below the threshold. Each of pulses 120 and 124 generates four triggering counts 144, while each pulse of corresponding depth in FIG. 6 generates only two triggering counts 144. However, the high velocity fluid stream results in four triggering pulses 128-134 in the same time span that the low velocity stream yields two triggering pulses 120 and 124. In each case the total triggering count (indicating particle concentration) is eight. Accordingly, the factors of decreased pulse width and increasing pulse frequency off-set one another. This yields a particle concentration measurement independent of fluid stream velocity.

A feature of the present invention arises because the output of threshold setting amplifier 104 is based on the output of amplifier 92. This ensures that threshold voltage 107 is a constant percentage of the nominal voltage. Consequently, device 16 responds consistently to particles of various sizes, despite any variations in the amount of light received by detector 84, for example due to variations in the output of LED 80, connector coupling efficiency, alignment of optical fibers 28 and 30 in the probe head, or a soiling of optical fiber faces 66 and 68.

Thus, calibration of the device is independent of the amount of light to detector 84, and depends only on the physical dimensions of the cylindrical particle sensing volume. These dimensions depend on the width of gap 74 and the diameter of optical fiber cores 32 and 38. All of these dimensions can be repeated with a high degree of precision from one device to another, eliminating the need to individually calibrate each device.

Figure 7:
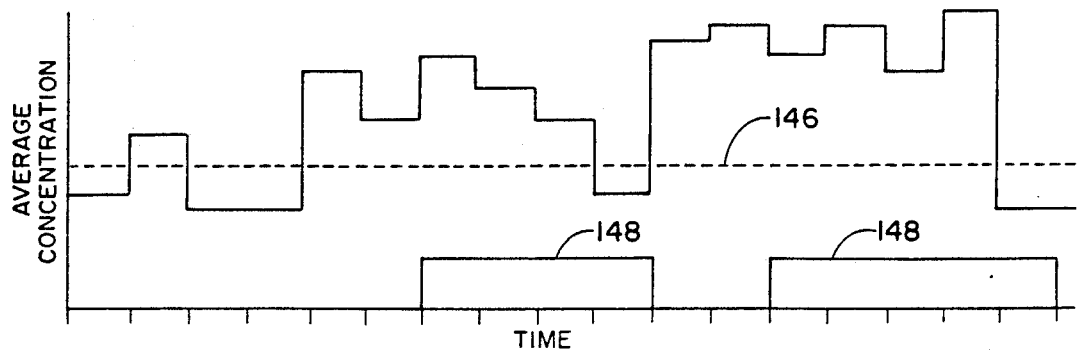
FIG. 7 is a timing diagram illustrating an alarm feature of the device.

FIG. 7 illustrates digital signal processing in circuit 118 to generate an alarm indication that the particulate concentration in a fluid flow is unacceptably high. Triggering counts 144, generated whenever a particle of sufficient size is within the particle sensing volume, are averaged over predetermined periods of time, to avoid false triggering from momentary spikes or aberrations in aerosol concentration. In particular, it is seen in FIG. 7 that the triggering counts are summed over consecutive time spans, e.g. one second each. The broken line at 146 indicates a threshold triggering count level. One-second counts at or below this level correspond to an acceptable particle concentration. One-second counts above the triggering level are stored, and an alarm is triggered, as indicated at 148, responsive to two consecutive one-second counts exceeding the threshold trigger level. Alarm light 26 remains active so long as one-second counts continue to exceed the threshold trigger level, going inactive after the first acceptable one-second count. It is to be appreciated that different applications may require a different period than one second for count summing, an accumulation period different than two seconds, etc.

Figure 8:
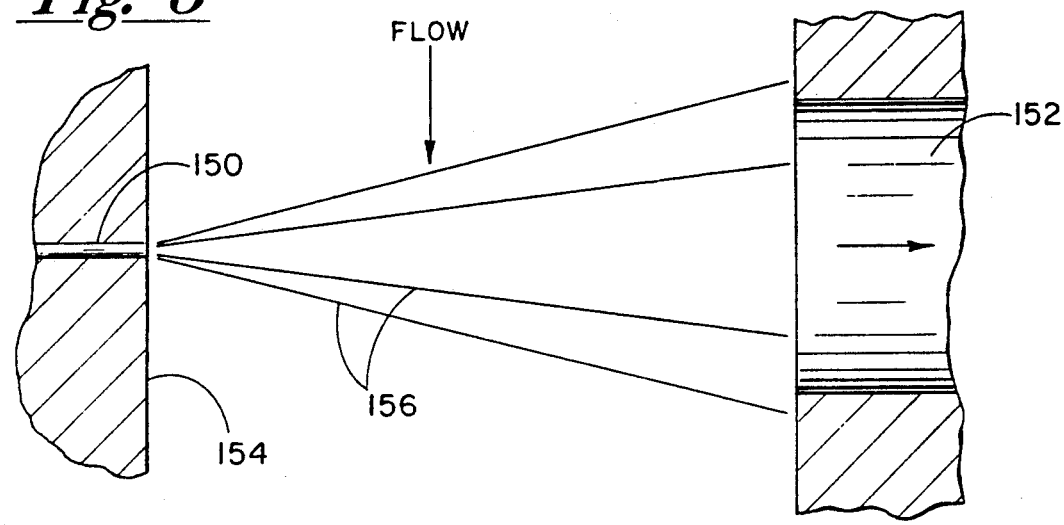
FIGS. 8 and 9 illustrate alternative embodiment devices.

FIG. 8 illustrates the confronting ends of a transmitting optical fiber 150 and a collecting optical fiber 152 fixed in a probe 154 of a second embodiment single particle sensing device. Collecting fiber 152 has the previously noted core diameter of 200 microns, while transmitting optical fiber 150 is substantially smaller, with a core diameter of about three microns. Fibers 150 and 152 are axially aligned, and the gap width is approximately one mm. The preferred light source is a laser diode (not shown). A beam of light 156 diverges as it exits transmitting fiber 150, yet substantially all of the beam is received within collecting optical fiber 152 due to its size. The particle sensing volume is equivalent to beam 156, and has the shape of a truncated cone. Enlarging collecting fiber 152 would not increase the particle sensing volume. However, a smaller collecting fiber would reduce the particle sensing volume. Thus, depending on the collecting fiber diameter, the particle sensing volume is defined either by the entire beam, or by a truncated cone with opposite ends defined by the respective fiber cores.

Figure 9:
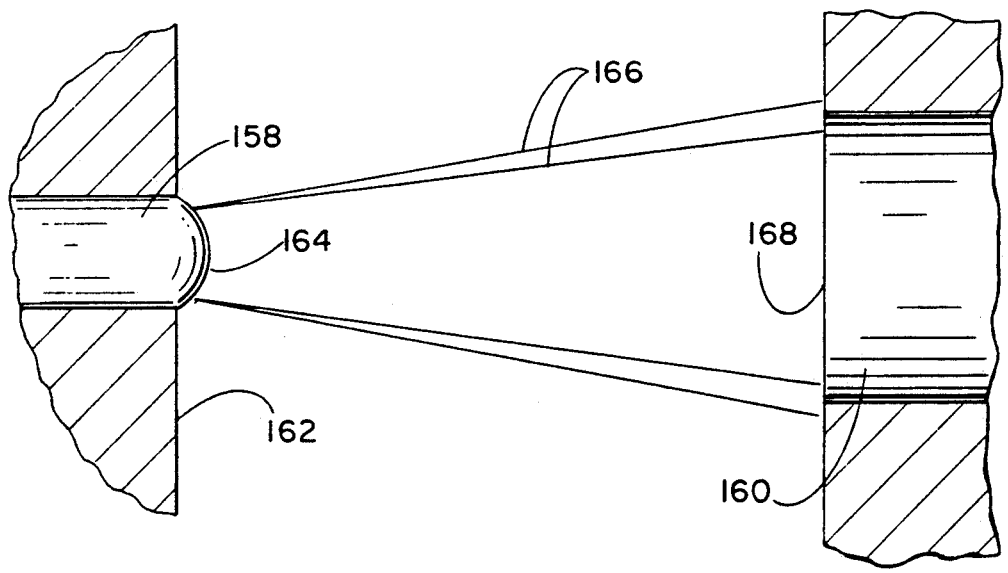

FIG. 9 illustrates the respective confronting end portions of a transmitting optical fiber 158 and a collecting optical fiber 160 fixed within a probe 162 of a third embodiment particle sensing device. An end or face 164 of the transmitting fiber is convex in the direction facing the collecting fiber, which tends to partially collimate a beam of light 166 exiting the transmitting fiber, which results in a greater portion of the light from fiber 158 entering collecting fiber 160. This advantage of a convex end for the transmitting optical fiber must be weighed against the greater tendency of such face to become soiled by particulates in the fluid stream, as compared to the flat, co-planar faces of the previous embodiments.

FIG. 10 illustrates the use of a single particle sensing device 170, e.g. like device 16, in a road construction vehicle 172. The vehicle includes a seat 174 for the operator, a steering wheel 176 and console 178. One of the vehicle wheels is shown at 180. The vehicle is powered by an internal combustion engine 182. The required combustion air is provided to the engine through an air intake duct 184, air being drawn into the engine by piston displacement. A filter 186 is installed along duct 184 to reduce the particulate concentration of air entering engine 182. An electronics package 188 is mounted beneath console 178, remote from a probe head 190. A jacket 192 surrounds and protects the transmitting and collecting optical fibers over the distance from probe head 190 to electronics package 188. A substantially direct path for the optical fibers is illustrated for convenience. However, the fibers and jacket 192 are sufficiently compliant to enable a convoluted or serpentine path, if required by the engine and surrounding equipment under the hood of vehicle 172. Probe head 190 is mounted by inserting the casing through an appropriately sized opening in duct 184, whereupon the mounting flange is secured to the duct on the outside. As noted previously, the voltage threshold can be set to prevent particles below a predetermined minimum size from triggering the sensing device. The triggering count threshold level, and the predetermined time period over which a count must exceed the trigger threshold level, likewise can be adjusted to suit the vehicle.

In certain instances it is desirable to determine the efficiency of filter 186, by comparing the upstream and downstream particle concentrations. To this end, a second sensing device 194, again equivalent to device 16, is mounted to duct 184 upstream of the filter. Device 194 operates in substantially the same manner as downstream device 170, except that it is not connected to trigger and alarm. Rather, upstream device 194 and downstream device 170 generate respective counts in a circuit such as circuit 118, to indicate particle concentrations.

The arrangement in FIG. 10 features a number of advantages of particle sensing devices constructed in accordance with the present invention. For example, the relatively low particle concentrations downstream of filter 186 call for a single particle detector rather than a photometer. Probe head 190 is much smaller and much simpler in construction than conventional single particle detectors, allowing flexibility and ease in installation. The size, together with signal processing electronics that operate independently of air stream velocity, enable the placement of the probe head directly within the air stream. The probe head is preferably installed with its major plane or profile (FIG. 1) parallel with the flow of the fluid stream, and with the open end forming the particle sensing volume, upstream. So positioned, the probe head provides minimal interference with the fluid flow. The transmitting and collecting fibers provide all of the essential optics, there being no need for lenses or mirrors, and thus no need to adjust or align such components.

FIG. 11 illustrates respective confronting end portions of a transmitting optical fiber 196 and collecting optical fiber 198 fixed within a probe 200 of a fourth embodiment particle sensing device. The optical fiber end portions are not axially aligned. Rather, each fiber is off-set from an aligned orientation, i.e. horizontal as viewed in FIG. 11, by an angle A, preferably 10 degrees. Likewise, planar ends or faces of the fibers, indicated respectively at 202 and 204, are not transverse and parallel to one another, but instead are angularly off-set from the vertical position by an angle B, preferably 30 degrees. Respective surface portions 206 and 208 that surround the fibers are similarly angularly off-set, to be co-planar with the fiber faces.

The particle sensing volume formed by fibers 196 and 198 is shown in broken lines at 210. Due to the 30 degree angular off-set of each end or face, light emitted from (and collected by) optical fibers 196 and 198 is refracted in a manner to balance the 10 degree angular off-set of the fiber. This arrangement is based on use of optical fibers with an index of refraction equal to 1.48. Fibers having different indices of refraction would call for slightly different fiber orientations or off-set angles for the faces. In any event, with air flow in the direction indicated by the arrow at 212, the off-set permits a somewhat recessed mounting of the optical fibers. Respective upstream portions 214 and 216 of the probe thus tend to protect faces 202 and 204 from becoming soiled due to particles in the air stream.

The probe has no moving parts. The integral securing of the optical fiber ends within the aluminum probe provides a rugged probe head able to withstand shock and vibration, and temperature extremes ranging from cold outdoor temperatures to the high temperatures near an operating internal combustion engine. In fact, the present device has been found to operate successfully, under test conditions, in temperatures up to 350 degrees F. The confronting ends or faces of the optical fibers, being perpendicular to the air flow (or recessed as in FIG. 11) and co-planar with surrounding probe head structure, tend to stay clean longer and enhance the useful life of the sensing device.

What is claimed is:

1. An apparatus for detecting single particles in a gas stream, including:
   a transmitting fiber optic means and a collecting fiber optic means, each having first and second opposite ends;
   a light source optically coupled to the first end of the transmitting fiber optic means;
   a light detecting means optically coupled to the first end of the collecting fiber optic means;
   a mounting means for maintaining the transmitting and collecting fiber optic means along respective end portions thereof, to position the respective second ends within a gas stream, confronting one another, and spaced apart longitudinally from one another to define a gap in the gas stream; wherein at least a portion of the light exiting the transmitting fiber optic means crosses the gap and is received by the collecting fiber optic means for transmission to the detecting means, said portion of the light defining a particle sensing volume spanning the gap; and
   a signalling means coupled to the light detecting means, for generating an analog signal proportional to the amount of light sensed by the detecting means, said analog signal having a nominal level when the particle sensing volume is free of particles, and having a reduced level less than the nominal level whenever a particle suspended in the fluid stream passes through the particle sensing volume; and
   a means for generating a threshold signal having a threshold level less than the nominal level, and a means for generating a particle responsive output whenever a single particle of at least a minimum threshold size passes through said particle sensing volume.

2. The apparatus of claim 1 wherein:
said analog signal is an analog voltage signal having a nominal voltage level when the particle sensing volume is free of particles, and having a reduced voltage level less than the nominal level whenever a particle suspended in the gas stream occupies the particle sensing volume and thereby temporarily diminishes the amount of light received by the collecting fiber optic means.

3. The apparatus of claim 2 wherein:
said means for generating a threshold signal generates a threshold voltage less than said nominal voltage level, and wherein said means for generating a particle responsive output includes a first comparator means receiving said analog voltage signal and the threshold voltage, said first comparator means generating said particle responsive output as a first logic level whenever the analog signal is less than the threshold voltage, and a second logic level whenever the analog signal is greater than the threshold voltage.

4. The apparatus of claim 3 wherein:
said threshold voltage level is linearly proportional to the nominal voltage.

5. The apparatus of claim 3 further including;
a pulse generating means generating an electronic clocking signal comprised of clocking pulses, and a counting means incremented responsive to the first logic level and the clocking signal, the number of increments accumulated in the counting means per unit time providing an indication of particle concentration.

6. The apparatus of claim 2 further including:
a means for generating a minimum reference voltage corresponding to an acceptable minimum level of light received by the detecting means, and a second comparator means for receiving said analog signal and said second reference voltage and generating a low light output to trigger a low light indication when the analog signal is less than the minimum reference voltage.

7. The apparatus of claim 1 wherein:
the collecting fiber optic means receives less than all of the light emitted from the first fiber optic means, and wherein the particle sensing volume is defined by the respective transverse profiles of the respective second ends and the longitudinal dimension of the gap.

8. The apparatus of claim 7 wherein:
each of the transmitting and collecting fiber optic means comprises an elongate and cylindrical optical fiber, the fibers being axially aligned with one another and substantially equal in diameter.

9. The apparatus of claim 8 wherein:
each of the respective second ends is substantially smooth, flat and transverse.

10. The apparatus of claim 9 wherein:
said mounting means comprises a rigid casing.

11. The apparatus of claim 10 wherein:
the casing includes first and second transverse exterior surface portions adjacent the respective second ends, each surface portion co-planar with its respective one of the second ends.

12. The apparatus of claim 1 wherein:
said collecting fiber optic means collects substantially all of the light emitted by the transmitting fiber optic means, and said particle sensing volume coincides with the beam of light spanning the gap.

13. The apparatus of claim 12 wherein:
the respective second ends of the fiber optic means are substantially flat and transverse, and the diameter of the collecting fiber optic means is at least twenty times the diameter of the transmitting fiber optic means.

14. The apparatus of claim 12 wherein:
said second end of the transmitting fiber optic means is contoured to reduce the divergence of light emitted by the transmitting fiber optic means in the longitudinal direction toward the collecting fiber optic means.

15. The apparatus of claim 1 wherein:
said light source and said light detecting means are remote from the fluid stream.

16. The apparatus of claim 1 further including:
respective first and second fiber optic connectors for releasably coupling the light source and the first end of the transmitting fiber optic means, and the detecting means and the first end of the collecting fiber optic means.

* * * * *